United States Patent [19]

Moorehead

[11] 4,212,309
[45] Jul. 15, 1980

[54] BLOOD GAS SAMPLER

[75] Inventor: Harvey R. Moorehead, Salt Lake City, Utah

[73] Assignee: Ballard Medical Products, Inc., Midvale, Utah

[21] Appl. No.: 946,887

[22] Filed: Sep. 28, 1978

[51] Int. Cl.³ .............................................. A61B 5/14
[52] U.S. Cl. .................................... 128/766; 128/765; 128/218 P; 128/218 PA
[58] Field of Search ........ 128/218 P, 218 PA, 218 M, 128/218 R, 219, 220, 234, 276, 762–766

[56] References Cited

U.S. PATENT DOCUMENTS

| 772,114 | 10/1904 | Pappenheim | 128/218 PA |
|---|---|---|---|
| 1,649,022 | 11/1927 | Eisele | 128/218 PA |
| 3,016,896 | 1/1962 | Van Sickle | 128/218 P |
| 3,354,882 | 11/1967 | Coanda | 128/218 P |
| 3,661,152 | 5/1972 | Beich et al. | 128/235 |
| 3,890,956 | 6/1975 | Moorehead | 128/2 F |

FOREIGN PATENT DOCUMENTS

| 33770 | of 0000 | Fed. Rep. of Germany | 128/218 P |
| 1292787 | 4/1969 | Fed. Rep. of Germany | 128/218 P |
| 19848 | of 1912 | United Kingdom | 128/218 P |
| 1173433 | 12/1969 | United Kingdom | 128/218 P |

Primary Examiner—Kyle L. Howell
Attorney, Agent, or Firm—Lynn G. Foster

[57] ABSTRACT

A blood-gas sampler in the nature of a syringe comprising a hollow internally stepped cylindrical barrel and a coaxial stepped plunger having one or more nesting stepped seals at the leading end thereof, the assembly accommodating arterial blood aspiration causing retraction of the plunger within the barrel and discharge of blood from the hollow of the barrel caused by advancement of the plunger. A clip prevents inadvertent excessive retraction of the plunger during the blood aspiration and blood discharge phases.

5 Claims, 5 Drawing Figures

U.S. Patent  Jul. 15, 1980  4,212,309
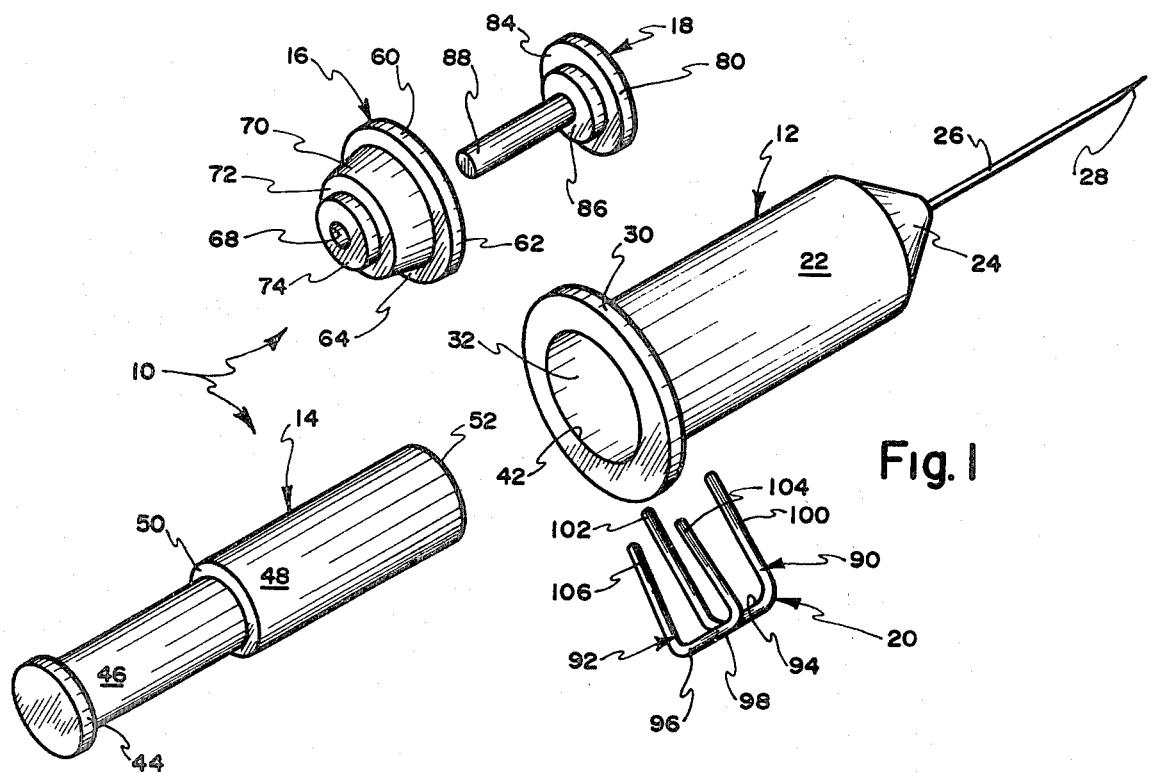
Fig. 1
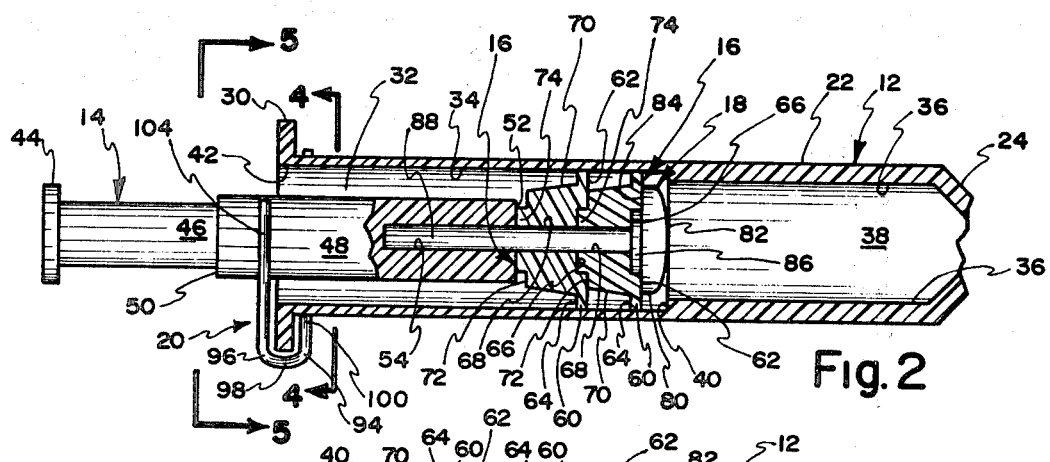
Fig. 2
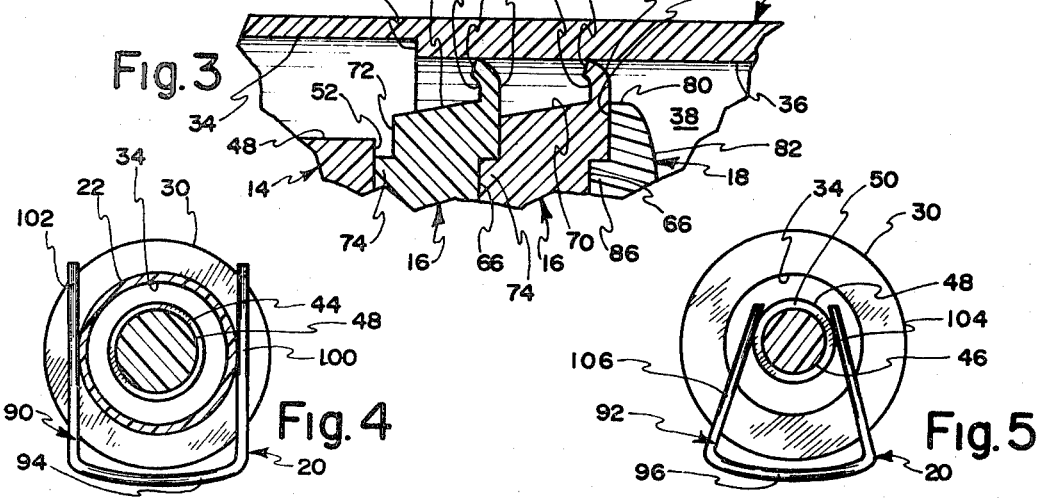
Fig. 3
Fig. 4
Fig. 5

BLOOD GAS SAMPLER

BACKGROUND

1. Field of Invention

The present invention relates generally to blood-gas analysis and more particularly to a blood-gas sampler comprising a syringe having novel seal, barrel and plunger fittings to accommodate entry of blood into the barrel under force of arterial pressure and discharge of blood from the barrel while avoiding seal set due to protracted shelf storage of the assembled syringe.

2. Prior Art

Prior art blood-gas sampling syringes have utilized relatively unsatisfactory seals interposed between the plunger and the barrel of the syringe. Most frequently the syringe barrels are glass, but occasionally of plastic. The mentioned seals are of a relatively hard elastomer and consist primarily of a single seal comprising two or three annularly enlarged rings each being deformed against the inside surface of the barrel creating a relatively wide high fricton sealing contact with the interior surface of the barrel. With such deformed seals storage over a protracted interval of time results in the elastomer of the seal taking a set. Thereafter, the required pliance no longer exists for the seal to conform to and follow the interior surface of the barrel. Accordingly, leaking of air and/or blood across the seal occurs, which renders inaccurate results when the blood-gas characteristics of the blood sample are tested. The subject matter of my prior U.S. Pat. No. 3,890,956 afforded the use of one sealing ring during aspiration and two during discharge but did not solve or attempt to solve the leakage problem due to seal set.

BRIEF SUMMARY AND OBJECTS OF THE PRESENT INVENTION

In its presently preferred form the present invention, in brief summary, comprises a blood-gas arterial syringe comprising a hollow interiorly stepped barrel and a plunger reciprocably situated within the barrel. One or more seals span between the leading end of the plunger and the interior surface of the barrel. Tandem seals, preferably of identical or like configuration may be used so that the magnitude of seal resistance is appropriate during blood aspiration and discharge. Each seal comprises a disc shaped annular wall or bead which sealingly contacts and conforms to the inside surface of the barrel and creates a movable fluid tight closure. An enlarged interior diameter at the trailing end of the barrel allows for storage of the assembled syringe with no more than negligible deformation in the seal bead to avoid deformed seal set due to storage and attendant leakage. A reduced interior diameter at the leading end of the barrel precipitates deformation in the seal only at a point in time when the syringe is used so that leakage is avoided. A clip may be utilized to prevent excessive plunger retraction during use of the syringe.

With the foregoing in mind, it is a primary object of the present invention to provide an improved blood-gas arterial sampling device.

A further paramount object of the present invention is the provision of a blood-gas arterial sampling syringe having improved seal construction.

A further primary object according to the present invention is the provision of a novel blood-gas sampler having improved barrel construction.

A further important object of the present invention is the provision of a blood-gas arterial sampling device which permits long shelf life of the assembled device without causing leakage precipitated by partial or complete set to take place in the seal thereof.

An additional significant object is the provision of a blood-gas syringe equipped with a clip to prevent excessive retraction during use.

These and other objects and features of the present invention will be apparent from the following detailed description, taken with reference to the accompanying drawings.

BRIEF DESCRIPTION OF THE DRAWINGS

FIG. 1 is an exploded perspective of a presently preferred blood-gas arterial sampling syringe according to the present invention;

FIG. 2 is a longitudinal cross section taken along the center line of the syringe of FIG. 1;

FIG. 3 is an enlarged fragmentary cross section illustrating the interior stepped barrel and the deformation induced in the seals during blood discharge;

FIG. 4 is a cross sectional view taken along line 4—4 of FIG. 2 illustrating the manner in which the anti-retraction clip is secured to the barrel; and FIG. 5 is a cross sectional view taken along line 5—5 of FIG. 2 illustrating the manner in which the anti-retraction clip functions to prohibit excessive retraction of the plunger following receipt of a blood sample.

DETAILED DESCRIPTION OF THE ILLUSTRATED EMBODIMENT

Reference is now made to the Figures wherein like numerals are used to designate like parts throughout. A presently preferred blood-gas sampling syringe, generally designated 10 is shown in the Figures. Syringe 10 is an assembly comprising a barrel 12, a plunger 14, at least one seal 16, a force fit seal retainer 18 and an anti-retraction clip 20, all parts being biologically inert. Preferably, when assembled, the syringe 10 is placed in a package, hermetically sealed and sterilized.

The barrel 12 is preferably light-transmitting and is made of glass or plastic material such that gas permeation from the exterior thereof is negligible. It is presently preferred that clear LEXAN injection molded as one piece be used since it does have negligible gas transmitting characteristics, is transparent and is less expensive than glass. The barrel 12 comprises a smooth elongated exterior cylindrical surface 22 of constant diameter, a tapered conical forward end 24 having a relatively small central port at which a needle 26 having a sharpened beveled tip 28 is conventionally secured. The barrel 12 exterior further comprises an outwardly projecting radial flange 30 to be gripped between the index and middle finger of the user. The barrel 12 also comprises a generally cylindrical stepped barrel interior 32 which comprises in large diameter bore portion 34 at the trailing end thereof and reduced diameter bore portion 36 at the leading end thereof. The opening 42 at the end of the portion 34 is of the same diameter as portion 34 and accommodates entry of the plunger 14. A radial shoulder 40 is interposed between the interior bore portions 34 and 36. The closed interior 38 of the syringe (FIG. 2) thus becomes a blood-receiving reservoir.

The plunger 14 is preferably of one-piece molded construction, and may be formed of polyproprionate. As illustrated, plunger 14 comprises a radially enlarged trailing end or handle 44, a reduced diameter cylindrical portion 46 and an enlarged diameter cylindrical portion 48 with a shoulder 50 separating the two cylindrical portions. The leading front surface 52 of the enlarged diameter cylindrical portion 48 is interrupted by an axially disposed blind bore 54 (FIG. 2), the diameter and length of which is predetermined for purposes yet to be explained. Generally speaking, the plunger 14 is intended to coaxially extend into the hollow interior 32 of the barrel and to accommodate retraction and extension during blood aspiration and blood discharge, respectively.

Each stepped nesting seal 16 is intended to be highly pliant and is preferably formed of soft vinyl or like material which is yieldable and readily conforms to surfaces against which it is forced. Each seal 16 comprises an enlarged sealing or wiping flange or annular bead 60 the diameter of which is equal to or slightly larger than the diameter of the enlarged interior bore 34 of the barrel 12 so that a low friction seal is created between flange 60 and the surface 34 with no more than negligible deformation in the flange 60, in the assembled but retracted position.

The flange 60 is interposed between a leading radial edge 62 and a trailing radial shoulder 64 of the seal 16. The leading radial surface 62 is centrally interrupted by an annular nesting recess 66 such that a uniform diameter central axial bore 68 opens at the center of the nesting recess 66.

The radial shoulder 64 merges with a rearwardly converging frusto-conical surface 70 which in turn merges with a reduced diameter radial shoulder 72. The trailing end of the seal 16 comprising a nesting projection 74 sized and shaped to be snugly received in the nesting recess 66 of an adjacent identically configurated seal, if used, or against the leading edge of the plunger 14. The trailing end of the central bore 68 of the seal emerges at the center of the nesting projection 74. The diameter of the axial throughbore 68 of each seal 16 is substantially the same as the diameter of the leading blind bore 54 of the plunger 14.

The force fit seal retainer 18 is of rigid plastic and comprises an exposed radial flange 80, which merges with an exposed rounded front face 82 and steps rearwardly across radial shoulder 84 to merge with nesting disc-shaped abutment 86 at the trailng end of the flange 80. The abutment 86 is sized and shaped so as to fit into the nesting recess 66 of the adjacent seal 16. Projecting integrally from the abutment 86 at the center thereof is an elongated rod 88 the diameter of which accommodates tight passage through the seal bore 68 and the plunger blind bore 54. Thus, rod 88, in the assembled condition, as best illustrated in FIG. 2, is force fit into and thereby retained in the blind bore 54. This in turn retains one or more seals 16 (two being illustrated) so that the annular sealing flange 60 thereof is disposed within the interior barrel portion 34. The length of the rod 88 is selected so that a substantial portion thereof is available to be firmly force fit into blind bore 54 with an additional length available to accommodate the number of seals 16 desired to create the requisite aspirating and discharge seal.

The anti-retraction clip 20 is formed of solid plastic having memory such as polypropylene and comprises a pair of U-shaped forks 90 and 92 the base 94 and 96 of each being integrally joined to the other by a bridge 98 to form a unitary clip. The U-shaped fork 90, in addition to the base 94 comprises a pair of upwardly directed parallel fingers 100 and 102. The space between the fingers 100 and 102 is an unstressed state slightly less than the outside diameter of the barrel 12 at smooth exterior cylindrical surface 22. Thus, when the fork 90 is force fit upwardly over the exterior 22 of the barrel 12, the converging fingers 100 and 102 are caused to be spread slightly thereby retaining the clip to the barrel due to the force of the memory of the material from which clip 20 is formed, as best illustrated in FIGS. 2 and 4. The length of the fingers 100 and 102 is preferably such that when the bridge 98 is juxtaposed the barrel flange 30, the tips of the fingers 100 and 102 are slightly above the top of the exterior barrel surface 22. Other clip arrangements and configurations could be used.

Either before or after the fork 90 is so secured to the barrel 12, the plunger (properly carrying one or more seals 16 retained by retainer 18) is inserted generally axially into the interior cylindrical portion 34. If the clip is in place, this is accomplished by manual force spreading the upwardly converging arms 104 and 106 to accommodate the plunger insertion. The plunger 14 is positioned so that the sealing flange 60 of each seal 16 is within the interior barrel surface 34 adjacent the shoulder 40. In this disposition, the manual spreading force exerted upon the fingers 104 and 106 is released and the memory of the anti-retraction clip causes the fingers 104 and 106 to close tightly against portion 48 of the plunger 14. Since the diameter of the plunger portion 48 is greater than the distance separating the arms 104 and 106 adjacent their terminal ends, a clamping force is exerted by the fork 92 against the end of the plunger portion 48 in this the storage position. This clamping force prevents inadvertent advancement of the plunger 14 together with the one or more seals 16 and seal retainer 18 into the reduced diameter barrel portion 36. It is to be appreciated that the interior surface 34 of the barrel, does not deform the seal during storage.

When it is desired to use the syringe 10, the plunger is advanced by manual application of force against the exposed flange 44 while gripping the barrel flange 38 between the index and middle finger until the seals are as far forward in barrel portion 36. The seal construction allows alignment of the plunger respecting the center line of the barrel without causing leakage across the seal. Said plunger advancement causes each seal 16 carried at the leading end of the plunger to travel over the shoulder 40 at the interior of the barrel, as best shown in FIG. 3. This plunger advancement causes the plunger portion 48 to clear the fork 92 and the fingers 104 and 106 come to rest against plunger portion 46 in essentially an unstressed state. (See FIG. 5.) Hence, the fingers 104 and 106 are aligned with plunger shoulder 50 to restrict the amount of plunger retraction which may later occur. Thus, for the first time independent of the length of time the syringe 10 was in storage or inventory, the seal or seals 16 are for the first time deformed. Accordingly, a firm seal is created between the deformed annular bead 60 of each seal and barrel interior surface 36. When the plunger is fully inserted into the barrel, the syringe 10 is ready to aspirate blood. This is accomplished by inserting the point 28 of the needle into the artery of the patient, which, due to arterial pressure, causes blood to fill the reservoir 38 as the plunger is caused to retract.

Plunger retraction is terminated when plunger shoulder 50 engages stationary clip fingers 104 and 106. Therefore, the fork 92 of the clip 20 prohibits the plunger 14, having once been advanced, from returning to its storage position. Thereafter, the needle is removed from the patient and the blood within the barrel reservoir 38 is discharged appropriately for blood gas testing by manually advancing the plunger.

The invention may be embodied in other specific forms without departing from the spirit or essential characteristics thereof. The present embodiment is therefore considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by U.S. Letters Patent is:

1. A method of obtaining a reliable blood specimen for analysis of gas characteristics using a syringe comprising the steps:
   assembling the syringe by placing a plunger partially within a barrel having a stepped bore so that a seal at the leading end of the plunger and unattached to the syringe barrel is not appreciably deformed by a larger trailing end barrel bore portion;
   storing the syringe in the mentioned assembled state for an interval of time;
   advancing the plunger further into the barrel causing the seal to engage and be sealingly deformed against but unattached to a smaller leading end barrel bore portion;
   retracting the plunger solely by arterial blood pressure following penetration of an artery thereby aspirating a blood specimen into the barrel without seal leakage;
   restricting seal displacement during aspiration to a length less than the length of the smaller leading barrel bore portion by engagement of external stop structure;
   discharging the sample, by exertion of manual force for testing of the gas characteristics thereof.

2. A method of obtaining a reliable blood specimen for analysis of the gas characteristics thereof using a blood-gas syringe comprising the steps of:
   exteriorly clamping a plunger of a blood-gas syringe in a pre-sampling storage disposition so that a seal at the leading end of the plunger is disposed within a barrel of the syringe;
   advancing the plunger within the barrel against the resistance of the clamping action a predetermined distance;
   further advancing the plunger another predetermined distance within the barrel to free the plunger of the clamping action;
   introducing a needle at the leading end of the syringe into an artery;
   retracting the plunger solely by arterial blood pressure free of the clamping action to aspirate a blood specimen into the barrel without seal leakage;
   stopping the plunger retraction by engagement between a portion of the plunger and the structure by which the clamping action is caused;
   discharging the sample, for blood-gas testing, by manual advancement of the plunger free of the clamping action.

3. A blood-gas arterial syringe comprising:
   a hollow barrel having means at the leading end receiving an arterial needle, said means comprising a relatively small diameter port whereby blood is communicated from an artery to the hollow of the barrel through the needle, the barrel further comprising a relatively large trailing inside diameter which opens to the rear of the barrel;
   a plunger extending through the rear opening and partially into the hollow of the barrel in the assembled position, the plunger comprising means at the exposed trailng end for manually advancing the plunger further into the hollow of the barrel and leading end means the maximum diameter of the plunger being sunbstantially less than all inside diametral portions of the hollow barrel with the exception of said small diameter port;
   diametrally enlarged barrel wall engaging head means, the exposed circumference of which is entirely elastomeric, the head means comprising seal means solely carried by connector means joined to the leading end means of the plunger and axially compressively engaging the seal means, the seal means being free of attachment to the barrel, the seal means comprising two or more contiguously nestable separate entirely elastomeric axially compressible seal elements, the seal elements being removably carried compressively in tandem at the leading end of the plunger, each seal element further comprising annular deflectable bead means having a diameter substantially greater than the inside diameter of the barrel adjacent the leading end thereof.

4. A blood-gas arterial syringe according to claim 3 wherein the interior of the barrel is stepped, the inside diameter toward the leading end thereof being smaller than the inside diameter thereof at the trailing end, wherein the seal means are free from attachment to the barrel and wherein the diameter of each bead means is substantially the same as the inside diameter at the trailing end of the barrel whereby during storage with the syringe assembled, the seal means are disposed with no more than negligible seal deformation within the larger trailing inside barrel diameter such that no deformation set occurs in any of the bead means and the seal elements are introduced successively into and the bead means thereof sealingly deflected against the smaller leading inside barrel diameter, by plunger advancement, for the first time immediately prior to use whereby inaccurate blood-gas analysis is avoided.

5. A blood-gas arterial syringe comprising:
   a hollow barrel having means at the leading end receiving an arterial needle, said means comprising a relatively small diameter port whereby blood is communicated from an artery to the hollow of the barrel the hollow barrel also comprising a rear opening and an interior step from a greater trailing inside barrel diameter to a lesser leading inside barrel diameter;
   a plunger extending through the rear opening and partially into the hollow of the barrel in the assembled position, the plunger comprising means at the exposed trailing end for manually advancing the plunger farther into the hollow of the barrel, leading end means, intermediate position retaining means and shoulder stop means;
   seal means carried by the leading end means of the plunger;
   clamp/stop means carried at the trailing end of the barrel comprising yieldable jaw means with memory which laterally clamp the position retaining means of the plunger in a storage position with the seal means within the greater trailing inside barrel diameter against inadvertent displacement of the plunger relative to the barrel prior to use and which is caused to axially abut the shoulder stop means to limit the withdrawal of the plunger to a specific distance in respect to the barrel during blood-gas aspiration.

* * * * *